United States Patent
Mitsuyama et al.

(10) Patent No.: US 8,158,800 B2
(45) Date of Patent: Apr. 17, 2012

(54) 4-{3-[4-(3-{4-[AMINO (BUTOXYCARBONYLIMINO) METHYL] PHENOXY} PROPYL)-1-PIPERIDINYL] PROPOXY}-N'-(BUTOXYCARBONYL) BENZAMIDINE CRYSTALS

(75) Inventors: Junichi Mitsuyama, Toyama (JP); Naokatsu Aoki, Toyama (JP)

(73) Assignee: Toyama Chemical Co., Ltd., Tokyo (JP)

( * ) Notice: Subject to any disclaimer, the term of this patent is extended or adjusted under 35 U.S.C. 154(b) by 114 days.

(21) Appl. No.: 12/667,179

(22) PCT Filed: Jul. 2, 2008

(86) PCT No.: PCT/JP2008/061944
§ 371 (c)(1),
(2), (4) Date: Jun. 24, 2010

(87) PCT Pub. No.: WO2009/005077
PCT Pub. Date: Jan. 8, 2009

(65) Prior Publication Data
US 2011/0046381 A1    Feb. 24, 2011

(30) Foreign Application Priority Data
Jul. 4, 2007 (JP) ................................. 2007-176106

(51) Int. Cl.
*C07D 211/26* (2006.01)

(52) U.S. Cl. ........................................................ 546/231
(58) Field of Classification Search .................. 546/231
See application file for complete search history.

(56) References Cited

U.S. PATENT DOCUMENTS

2008/0319016 A1    12/2008    Hayashi et al.

FOREIGN PATENT DOCUMENTS

| EP | 1 767 526 A1 | 3/2007 |
| EP | 2 070 536 A1 | 6/2009 |
| WO | 2006 003881 | 1/2006 |
| WO | 2007 074868 | 7/2007 |
| WO | WO 2008/044562 A1 | 4/2008 |

*Primary Examiner* — Janet Andres
*Assistant Examiner* — John Mabry
(74) *Attorney, Agent, or Firm* — Oblon, Spivak, McClelland, Maier & Neustadt, L.L.P.

(57) ABSTRACT

To provide novel crystals of 4-{3-[4-(3-{4-[amino(butoxycarbonylimino)methyl]phenoxy}propyl)-1-piperidinyl]propoxy}-N'-(butoxycarbonyl)benzamidine.
Means for Solving the Problems
The type II crystal, the type III crystal and the type IV crystal of 4-{3-[4-(3-{4-[amino(butoxycarbonylimino)methyl]phenoxy}propyl)-1-piperidinyl]propoxy}-N'-(butoxycarbonyl)benzamidine are useful as excellent drug substances of antifungal agents.

3 Claims, 2 Drawing Sheets

4-{3-[4-(3-{4-[AMINO (BUTOXYCARBONYLIMINO) METHYL] PHENOXY} PROPYL)-1-PIPERIDINYL] PROPOXY}-N'-(BUTOXYCARBONYL) BENZAMIDINE CRYSTALS

FIELD OF THE INVENTION

The present invention relates to novel crystals of 4-{3-[4-(3-{4-[amino(butoxycarbonylimino)methyl]phenoxy}propyl)-1-piperidinyl]propoxy}-N'-(butoxycarbonyl)benzamidine developed as an antifungal agent.

BACKGROUND ART

4-{3-[4-(3-{4-[amino(butoxycarbonylimino) methyl]phenoxy}propyl)-1-piperidinyl]propoxy}-N'-(butoxycarbonyl) benzamidine (hereinafter called as "Compound A") has potent activity against fungi including azole-resistant fungi, is excellent to oral absorption, is weak interaction with other drugs and has high safety, and is useful for an antifungal agent (Patent document 1).

The crystal of Compound A produced by manufacturing methods mentioned in patent documents 1 is called as "type I crystal".

[Patent document 1] International publication No. WO2007/074868 pamphlet

DISCLOSURE OF THE INVENTION

Problem to be Solved by the Invention

The crystal of Compound A having more excellent property as a drug substance, especially having the property that it is easy to handle, is strongly expected.

Means to Solve the Problem

Under these circumstances, the present inventors have conducted intensive research zealously, as a result, found that the crystal of Compound A having peaks at the positions of 5.8, 18.2, 20.9 and 24.7° on 2θ of the diffraction angle in the powder X-ray diffraction pattern (hereinafter called as "type II crystal"), the crystal of Compound A having peaks at the positions of 8.7, 12.0, 22.2 and 24.3° on 2θ of the diffraction angle in the powder X-ray diffraction pattern (hereinafter called as "type III crystal") and the crystal of Compound A having peaks at the positions of 9.8 and 23.5° on 2θ of the diffraction angle in the powder X-ray diffraction pattern (hereinafter called as "type IV crystal") are excellent as a drug substance because (1) the tapped density of which is high, (2) it is hard to be charged with electricity, (3) it is easy to handle, (4) the compression moldability is good, (5) it is hard to be sticking, and (6) the mass production of which is possible, and they had completed the invention.

Effect of the Invention

The crystals of the present invention, (1) the tapped density of which is high, (2) it is hard to be charged with electricity, (3) it is easy to handle, (4) the compression moldability of which is good, (5) it is hard to be sticking, and (6) the mass production of which is possible, and are useful for a drug substance.

BEST MODE FOR CARRYING OUT THE INVENTION

The present invention is described in detail as follows.

The present invention relates to the type II crystal having peaks at the positions of 5.8, 18.2, 20.9 and 24.7° on 2θ of the diffraction angle in the powder X-ray diffraction pattern, the type III crystal having peaks at the positions of 8.7, 12.0, 22.2 and 24.3° on 2θ of the diffraction angle in the powder X-ray diffraction pattern and the type IV crystal having peaks at the positions of 9.8 and 23.5° on 2θ of the diffraction angle in the powder X-ray diffraction pattern. These crystals of the present invention are not known at all until now, are not described in the patent document 1 at all, and are novel crystals. In addition, the characteristic peaks of the powder X-ray diffraction may change by conditions of measurement. Therefore, peaks of the powder X-ray diffraction of the compounds of the present invention are not interpreted strictly.

The manufacturing process of the compounds of the present invention is explained.

The type II crystal, for example, can be produced by a manufacturing process shown as follows.

[Manufacturing Process 1]

The type II crystal can be produced by suspending and stirring the type I crystal in solvents.

For solvents used in this production, ketones such as methylethylketone and methylisobutylketone; alcohols such as 2-propanol and butanol; esters such as ethyl acetate and butyl acetate; ethers such as 1,4-dioxane; aliphatic hydrocarbons such as heptane and cyclohexane; S-oxides such as dimethyl sulfoxide; aromatic hydrocarbons such as toluene; nitriles such as acetonitrile; amides such as N,N-dimethylformamide and N-methylpyrrolidone; and water, are given. These solvents may be used in combination.

The amount of the solvent used is desirably 1 to 100 times volume (v/w) as the standard of the weight of the type I crystal, and is preferably 5 to 10 times volume (v/w).

The temperature of stirring is desirably 50 to 150° C., and is preferably 70 to 120° C.

The time of stirring is desirably 0.1 to 5 hours, and is preferably 0.5 to 3 hours.

According to the method described above, the type II crystal can be produced by use of the type III crystal or the type IV crystal, both of which are described hereinafter, instead of the type I crystal.

The type III crystal, for example, can be produced by a manufacturing process shown as follows.

[Manufacturing Process 2]

The type III crystal can be produced by suspending and stirring the type I crystal in aqueous solvents.

For solvents used in this production, ketones such as methylethylketone; alcohols such as butanol; esters such as ethyl acetate; ethers such as tetrahydrofuran; aromatic hydrocarbons such as toluene; and halogenated hydrocarbons such as chloroform, are given. These solvents may be used in combination.

The amount of the aqueous solvent used is desirably 1 to 100 times volume (v/w) as the standard of the weight of the type I crystal, and is preferably 2 to 10 times volume (v/w).

The ratio of solvent and water is desirably within the range in which (solvent)/(water) is 99/1 to 30/70, and is preferably within the range in which (solvent)/(water) is 90/10 to 50/50.

The temperature of stirring is desirably 10 to 40° C., and is preferably 20 to 30° C.

The time of stirring is desirably 0.1 hours to 30 days, and is preferably one hour to 14 days.

According to the method described above, the type III crystal can be produced by use of the type II crystal instead of the type I crystal.

[Manufacturing Process 3]

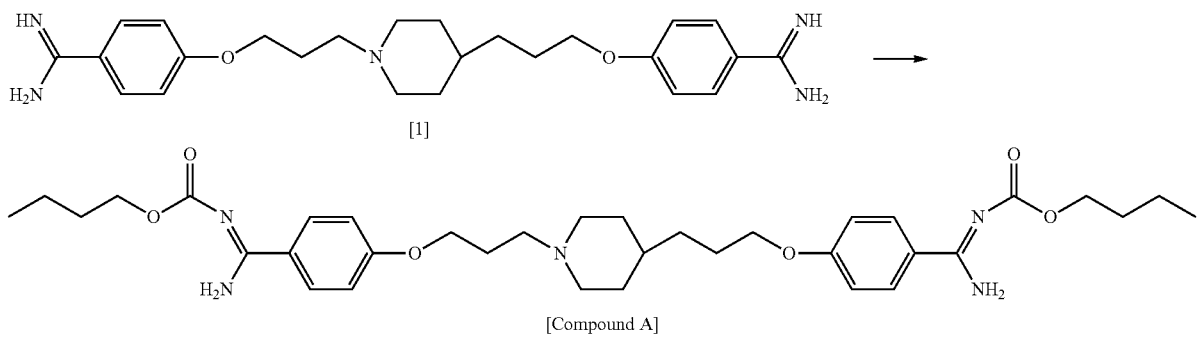

[Compound A]

The type III crystal can be produced by crystallization after the compound of formula [1] is reacted with a reactive derivative in the presence or absence of a base.

(1) Compound A can be produced by reacting the compound of formula [1] with a reactive derivative in the presence or absence of a base.

For solvents used in this reaction, for example, ketones such as methylethylketone; esters such as ethyl acetate; ethers such as tetrahydrofuran; aromatic hydrocarbons such as toluene; halogenated hydrocarbons such as chloroform; amides such as N,N-dimethylformamide; and water, are given. These solvents may be used in combination.

For reactive derivatives, for example, butyl chloroformate, butyl 4-nitrophenyl carbonate and butyl 1H-imidazole-1-carboxylate, are given. These reactive derivatives may be used after preparation in situ without isolating.

For bases used in this reaction, if desired, for example, metal alkoxides such as sodium methoxide, sodium ethoxide, potassium tert-butoxide, and sodium tert-butoxide; inorganic bases such as sodium hydroxide, potassium hydroxide, sodium hydrogen carbonate, sodium carbonate, potassium carbonate, sodium hydride, and potassium hydride; and organic bases such as triethylamine, N,N-diisopropylethylamine, 1,8-diazabicyclo[5.4.0]undec-7-ene (DBU) and pyridine are given.

The amounts of the reactive derivative and the base may be 2- to 100-fold moles, desirably 2- to 10-fold moles based on the compound of formula [1].

This reaction may be conducted at −20 to 100° C., desirably 20 to 80° C. for one minute to 24 hours.

This reaction may be conducted preferably at 20 to 80° C. for one minute to 7 hours.

(2) After the reaction, Compound A produced is extracted from the reaction mixture by general methods.

For extracting solvents used, for example, ketones such as methylethylketone; esters such as ethyl acetate; ethers such as tetrahydrofuran; aromatic hydrocarbons such as toluene; and halogenated hydrocarbons such as chloroform, are given. These solvents may be used in combination.

The temperature of extracting is not particularly limited, but is desirably 50 to 80° C.

(3) The type III crystal can be produced by crystallization after the seed crystal of the type III crystal is added to the extraction solution.

The condition of crystallization is desirably to cool from 50 to 80° C. to 0 to 10° C. for 12 to 24 hours.

The type IV crystal, for example, can be produced by a manufacturing process shown as follows.

[Manufacturing Process 4]

The type IV crystal can be produced by suspending and stirring the type II crystal in solvents.

For solvents used in this production, ketones such as acetone are given.

The amount of the solvent used is desirably 1 to 100 times volume (v/w) as the standard of the weight of the type II crystal, and is preferably 2 to 30 times volume (v/w).

The temperature of stirring is desirably 0 to 10° C.

The time of stirring is desirably 1 to 30 days, and is preferably 7 to 30 days.

In the case that the compounds of the present invention (the type II crystal, the type III crystal and the type IV crystal) are used as a medicine, they can be used alone or mixed.

Being used as a medicine, the compound of the invention may generally be properly mixed with pharmaceutical auxiliaries such as an excipient, a carrier, and a diluent which are used for formulation, and which can be orally or parenterally administered in the form of tablets, capsules, powders, syrups, granules, pills, suspensions, emulsions, solutions, powder preparations, suppositories, eye drops, nasal drops, ear drops, patches, ointments, or injections, according to ordinary methods. In addition, the administration method, dosage, and administration frequency can be properly selected depending on the age, body weight and symptoms of a patient. Typically, 0.01 to 1,000 mg/kg thereof may be administered orally or parenterally (e.g., by injection, drip infusion, or rectal administration) to an adult once or in several divided portions in a day.

Next, the utility of the compounds of the present invention is explained with the following tests.

For test materials, the compounds of the present invention (the type II crystal, the type III crystal and the type IV crystal) and the type I crystal were used.

TEST EXAMPLE 1

Tapped Density

The test materials passed through a sieve (18 mesh) were filled into a measuring cylinder and the weight W(g) of the filled test materials was measured. Next, the measuring cylinder containing the test materials was mechanically tapped 180 times by a powder characteristic measuring device (a powder tester PT-E, Hosokawa Micron Corporation). After tapping, the volume V1 (mL) of the tapped test materials was measured. By the following formula, the tapped density (g/mL) was calculated. The results are shown in Table 1.

Tapped density (g/mL)=W/V1

TABLE 1

|  | Tapped density (g/mL) |
| --- | --- |
| Type I crystal | 0.22 |
| Type II crystal | 0.40 |
| Type III crystal | 0.45 |
| Type IV crystal | 0.47 |

The tapped density of the compounds of the present invention was higher than that of the type I crystal.

TEST EXAMPLE 2

Surface Potential

The following test was conducted in a thermo-hygrostat (25° C., 50% RH).

The test materials were set in a sample plate (SUS304, the surface was ground by a buff400, the volume: about 6 mL, the depth: 3 mm, cylindrical, the upper aspect was opened), and was charged by corona discharge (the corona voltage: −4 kV) from an impressed voltage device for 2 minutes (the distance between the impressed voltage device and the sample plate: 30 mm). After charging, the surface potential of the test materials was measured (the distance between the sensor and the sample: 5 mm). The results are shown in Table 2.

Thermo-hygrostat: KCL-2000, EYELA CORPORATION
Surface potential measurement device: SK-200, KEYENCE CORPORATION
Impressed voltage device: SJ-G036, KEYENCE CORPORATION
Data logger: AD-DIO Card Bus, Interface Corporation

TABLE 2

|  | Surface potential (kV) |
| --- | --- |
| Type I crystal | −2.3 |
| Type III crystal | −1.9 |
| Type IV crystal | −1.3 |

The surface potential of the compounds of the present invention was lower than that of the type I crystal, and consequently the compounds of the present invention were hard to be charged with static electricity.

TEST EXAMPLE 3

Sticking Test

Tablets (flat-shaped, the diameter 8.5 mm) containing 200 mg of the test materials were prepared by using a tableting process analyzer (Tab Flex TAB-10, OKADA SEIKO CO., LTD.) (the loading pressure: 10 kN). Next, the scraper pressure was measured when the tablets were pushed out by a scraper. The results are shown in Table 3.

TABLE 3

|  | Scraper pressure (kN) |
| --- | --- |
| Type I crystal | 7.2 |
| Type II crystal | 2.9 |
| Type III crystal | 1.9 |
| Type IV crystal | 2.9 |

The scraper pressure of the compounds of the present invention was smaller than that of the type I crystal. It was suggested that the compounds of the present invention have the property to be hard to cause a sticking problem (a tableting problem by metal adhesion of powders) in comparison with the type I crystal.

TEST EXAMPLE 4

Adhesion Test to a Metal Cup 5 g of the test materials passed through a sieve (18 mesh) are filled in a metal cup (SUS304, the internal diameter: 65 mm, the volume: about 200 mL), and then the test materials were removed by turning over the cup. The weight of the test materials adhering on the surface of the cup was measured. The results are shown in Table 4.

TABLE 4

|  | Adhering amount (mg) |
| --- | --- |
| Type I crystal | 70 |
| Type II crystal | 17 |
| Type III crystal | 22 |
| Type IV crystal | 40 |

The adhering amount of the compounds of the present invention was smaller than that of the type I crystal. It was suggested that the compounds of the present invention have the property to be hard to adhere to a metal cup.

TEST EXAMPLE 5

Compression Moldability Test

Tablets (flat-shaped, the diameter: 8.5 mm) containing 200 mg of the test materials were prepared by using a tableting process analyzer (Tab Flex TAB-10, OKADA SEIKO CO., LTD.) (The loading pressure: 5 and 10 kN). Next, the breaking strength of the tablets was measured by a tablet hardness tester (PC-30, OKADA SEIKO CO., LTD.). The results are shown in Table 5.

TABLE 5

|  | Hardness (N) | |
| --- | --- | --- |
|  | Loading pressure 5 kN | Loading pressure 10 kN |
| Type I crystal | 56 | 57 |
| Type II crystal | 63 | 94 |
| Type III crystal | 66 | 95 |

The hardness of the tablets of the type I crystal did not change even if the loading pressure increased. On the other hand, the hardness of the tablets of the compounds of the present invention was higher than that of the type I crystal. In addition, the hardness of the tablets of the compounds of the present invention was increased as the loading pressure increased. The compression moldability of the tablets of the compounds of the present invention was superior to that of the type I crystal.

TEST EXAMPLE 6

Mouse *Candida* Infection Model Test (Oral Administration)

*Candida albicans* TIMM1623, which was obtained from overnight cultures grown on Sabouraud dextrose agar (SDA) plates at 35° C., was suspended in sterile physiological saline, then diluted to prepare a suspension of inoculum organism.

Transient immunosuppression in mice (four-week-old, 5 mice/group) was induced by intraperitoneal treatment with 200 mg/kg cyclophosphamide 4 days before the infection and with 100 mg/kg cyclophosphamide 1 day after the infection. Infection was induced by the intravenous inoculation of 0.2 mL of the cell suspension of *Candida albicans* TIMM1623 (about 3×10$^4$ CFU/mouse) via the lateral tail vein. The test compound was dissolved in 0.1 mol/L hydrochloric acid, diluted by sterilized water and orally administered at 1 mg/kg of mouse body weight. The therapy was started at 2 hours after infection and carried out once daily for 4 days. The equivalent amount of sterilized physiological saline was administered to the group to which no test compound was administered. The survival number of mice was observed and recorded for 14 days.

As a result, all mice died in a group to which no test compound was administered, but 80% of mice survived in the group to which the compounds of Reference example 1, Example 1, Example 2 and Example 4 was administered.

The compounds of Reference example 1, Example 1, Example 2 and Example 4 had an excellent therapeutic effect.

Next, the present invention is explained with reference examples and examples, but the present invention is not limited to these.

Conditions of measurement for the powder X-ray diffraction

Anti-cathode: Cu, tube voltage: 40 kV, tube current: 40 mA

The values of peaks in an infrared absorption spectrum, which were useful to distinguish crystals, were listed.

REFERENCE EXAMPLE 1

(Production of the Type I Crystal, Patent Document 1, Example 3-2)

To an N,N-dimethylformamide (15 mL) solution of 1.82 g of butyl 4-nitrophenyl carbonate was added 1.50 g of 4-{3-[4-(3-{4-[amino(imino)methyl]phenoxy}propyl}-1-piperidinyl]propoxy}benzamidine at room temperature, which was then stirred at the same temperature for 2 hours. Chloroform and water were added to the reaction mixture. The organic layer was separated, washed sequentially with a 5% potassium carbonate aqueous solution (2 times) and a saturated sodium chloride aqueous solution, and then dried over anhydrous magnesium sulfate, followed by distilling off the solvent under reduced pressure. The resultant residue was purified by silica gel column chromatography (eluent; chloroform:methanol=4:1). The resultant solid matter was dissolved in chloroform, washed sequentially with a 5% potassium carbonate aqueous solution (2 times) and a saturated sodium chloride aqueous solution, and then dried over anhydrous magnesium sulfate, followed by distilling off the solvent under reduced pressure to give 1.39 g of the type I crystal of 4-{3-[4-(3-{4-[amino(butoxycarbonylimino)methyl]phenoxy}propyl)-1-piperidinyl]propoxy}-N'-(butoxycarbonyl)benzamidine as white solid forms.

$^1$H-NMR(CDCl$_3$) .δ value: 0.95(6H, t, J=7.3 Hz), 1.20-1.50(9H, m), 1.60-2.05(12H, m), 2.45-2.54(2H, m), 2.90-3.00(2H, m), 3.99(2H, t, J=6.6 Hz), 4.06(2H, t, J=6.3 Hz), 4.16(4H, t, J=6.8 Hz), 6.88-6.96(4H, m), 7.82-7.88(4H, m).

The powder X-ray diffraction data were shown in Table 6, and the pattern was shown in FIG. 1.

IR(ATR): 1075, 1026 cm$^{-1}$

TABLE 6

| 2θ | d | Relative intensity |
|---|---|---|
| 6.84 | 12.92 | 74 |
| 10.20 | 8.67 | 29 |
| 17.31 | 5.12 | 39 |
| 18.06 | 4.91 | 55 |
| 22.07 | 4.02 | 100 |
| 22.81 | 3.89 | 59 |
| 24.74 | 3.60 | 34 |
| 26.33 | 3.38 | 21 |
| 26.97 | 3.30 | 27 |
| 27.76 | 3.21 | 30 |

EXAMPLE 1

(Production of the Type II Crystal)

To ethyl acetate (1630 mL) was added 163 g of the type I crystal, which was then refluxed for 30 minutes. After the reaction mixture was cooled to 60 to 65° C., it was stirred at the same temperature for 30 minutes. The solid matter was filtrated and collected, and air-dried to give 139 g of the type II crystal.

The powder X-ray diffraction data were shown in Table 7, and the pattern was shown in FIG. 2.

IR(ATR): 1071, 1048 cm$^{-1}$

TABLE 7

| 2θ | d | Relative intensity |
|---|---|---|
| 5.79 | 15.24 | 49 |
| 8.94 | 9.88 | 29 |
| 11.84 | 7.47 | 15 |
| 16.81 | 5.27 | 21 |
| 18.18 | 4.87 | 89 |
| 20.87 | 4.25 | 100 |
| 21.60 | 4.11 | 24 |
| 24.66 | 3.61 | 96 |
| 25.24 | 3.53 | 29 |
| 27.94 | 3.19 | 20 |

EXAMPLE 2

(Production of the Type III Crystal)

Methylethylketone (435 mL) and water (435 mL) were added to 87.2 g of the type I crystal, and it was stirred at room temperature for 24 hours. The solid matter was filtrated and collected, and air-dried to give 69.8 g of the type III crystal.

The powder X-ray diffraction data were shown in Table 8, and the pattern was shown in FIG. 3.

IR(ATR): 1072, 1054, 1018 cm$^{-1}$

TABLE 8

| 2θ | d | Relative intensity |
|---|---|---|
| 8.74 | 10.10 | 19 |
| 11.97 | 7.39 | 9 |
| 22.17 | 4.01 | 100 |
| 24.33 | 3.66 | 12 |

EXAMPLE 3

(Production of the Type III Crystal)

To a methylethylketone (1800 mL) solution of 231 g of imidazole was added 232 g of butyl chloroformate at room temperature, which was then left the same temperature overnight. Water (1440 mL), 360 g of 4-{3-[4-(3-{4-[amino (imino)methyl]phenoxy}propyl)-1-piperidinyl]propoxy}benzamidine trihydrochloride pentahydrate and ethyl acetate (360 mL) were added to the reaction mixture, and it was refluxed for 3 hours. The organic layer was separated at 60 to 70° C., washed with water, and methylethylketone (720 mL) was added to the organic layer. The insoluble matter was filtered off at 60 to 70° C., and the cake was washed with methylethylketone (720 mL). The filtrate and the washings were combined, which was heated and dissolved. The seed crystal of the type III crystal was added at 40 to 45° C., and it was stirred at the same temperature for 2 hours. After it was stirred to 5° C. for 14 hours, the solid matter was filtrated and collected to give 333 g of the type III crystal.

IR and the powder X-ray diffraction pattern accorded with the value of example 2.

EXAMPLE 4

(Production of the Type IV Crystal)

Acetone (4 mL) was added to 0.20 g of the type II crystal, and it was stirred at 5 to 10° C. for a week. The solid matter was filtrated and collected, and air-dried to give 0.17 g of the type IV crystal.

The powder X-ray diffraction data were shown in Table 9, and the pattern was shown in FIG. 4.

IR(ATR): 1094, 1070, 1056, 1019 cm$^{-1}$

TABLE 9

| 2θ | d | Relative intensity |
|---|---|---|
| 9.79 | 9.02 | 8 |
| 13.83 | 6.40 | 5 |
| 14.65 | 6.04 | 5 |

TABLE 9-continued

| 2θ | d | Relative intensity |
|---|---|---|
| 17.05 | 5.20 | 24 |
| 19.61 | 4.52 | 12 |
| 23.49 | 3.78 | 100 |

INDUSTRIAL APPLICABILITY

Figure 1:
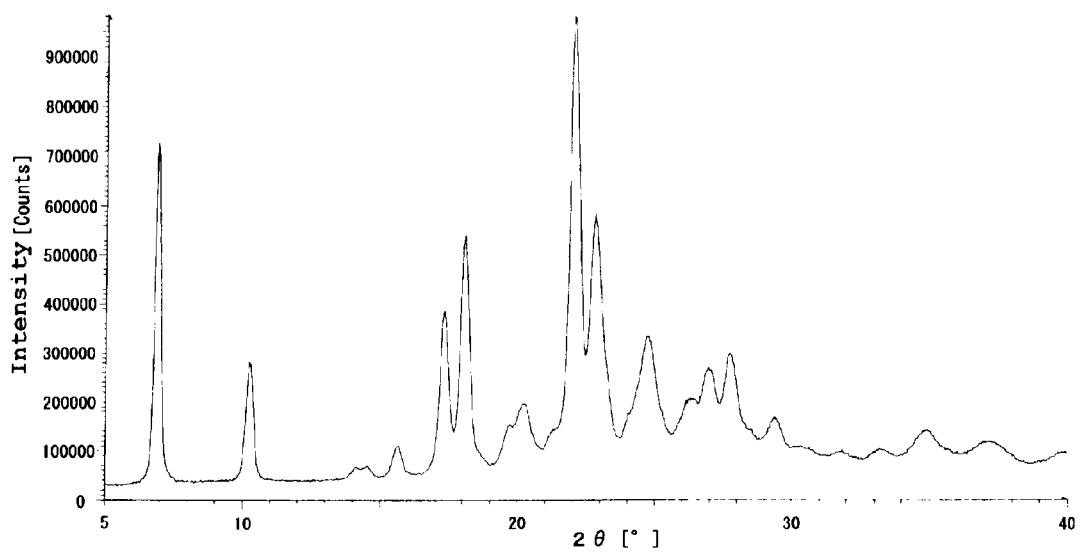
FIG. 1 represents the powder X-ray diffraction pattern of the type I crystal.
Figure 2:
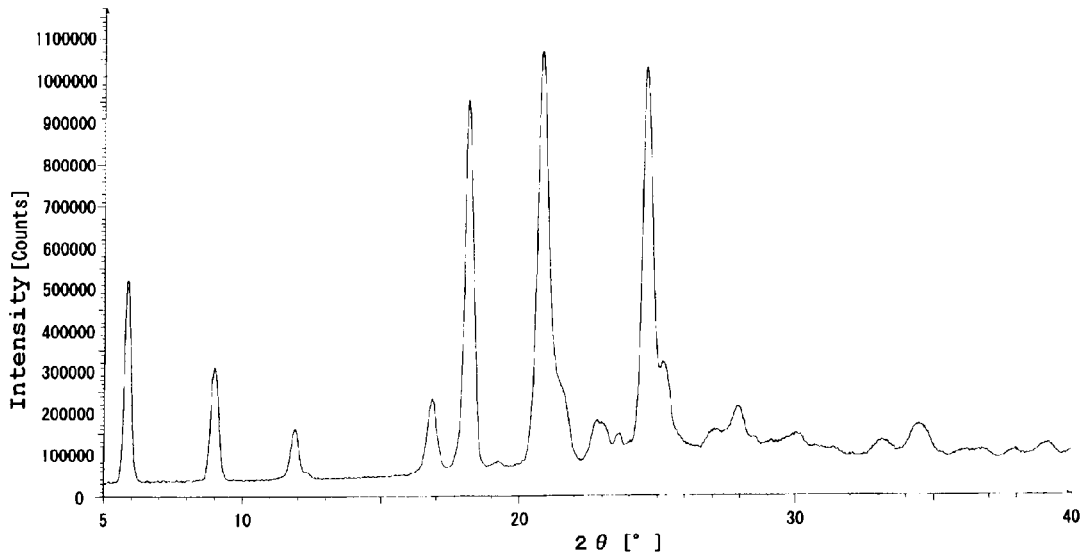
FIG. 2 represents the powder X-ray diffraction pattern of the type II crystal.
Figure 3:
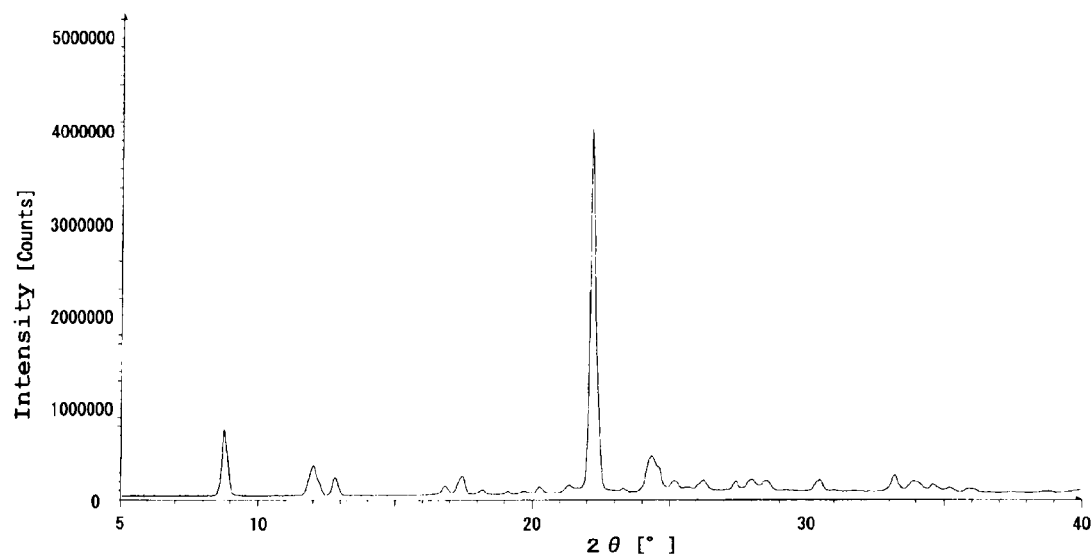
FIG. 3 represents the powder X-ray diffraction pattern of the type III crystal.
Figure 4:
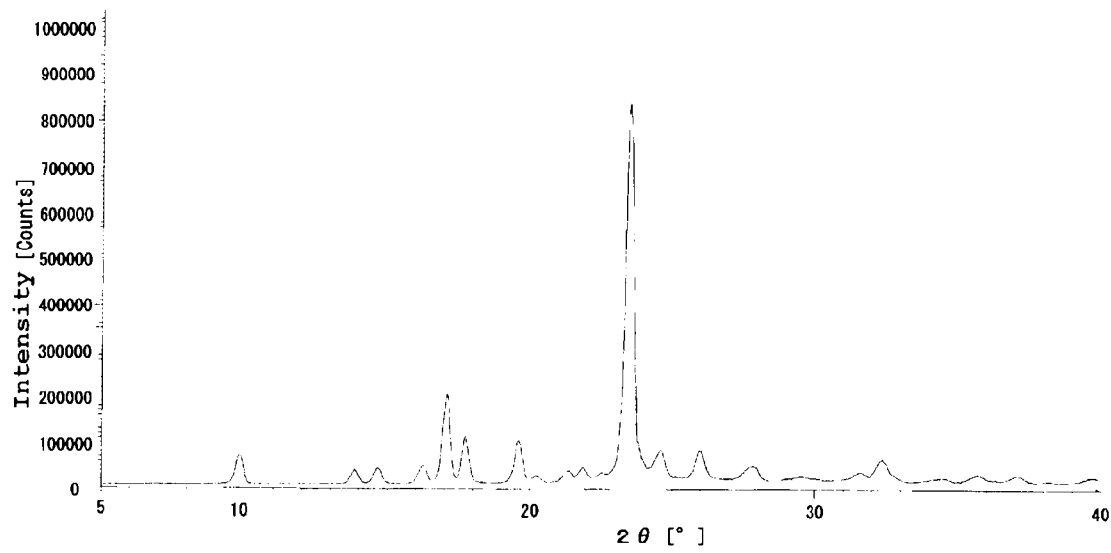
FIG. 4 represents the powder X-ray diffraction pattern of the type IV crystal.

The crystals of the present invention, (1) the tapped density of which is high, (2) it is hard to be charged with electricity, (3) it is easy to handle, (4) the compression moldability of which is good, (5) it is hard to be sticking, and (6) the mass production of which is possible, and are useful for a drug substance.

The invention claimed is:

1. The crystal of 4-{3-[4-(3-{4-[amino(butoxycarbonylimino)methyl]phenoxy}propyl)-1-piperidinyl]propoxy}-N'-(butoxycarbonyl)benzamidine having peaks at the position of 5.8, 18.2, 20.9 and 24.7° on 2θ of the diffraction angle in the powder X-ray diffraction pattern.

2. The crystal of 4-{3-[4-(3-{4-[amino(butoxycarbonylimino)methyl]phenoxy}propyl)-1-piperidinyl]propoxy}-N'-(butoxycarbonyl)benzamidine having peaks at the position of 8.7, 12.0, 22.2 and 24.3° on 2θ of the diffraction angle in the powder X-ray diffraction pattern.

3. The crystal of 4-{3-[4-(3-{4-[amino(butoxycarbonylimino)methyl]phenoxy}propyl)-1-piperidinyl]propoxy}-N'-(butoxycarbonyl)benzamidine having peaks at the position of 9.8 17.05, 19.61 and 23.5° on 2θ of the diffraction angle in the powder X-ray diffraction pattern.

* * * * *